(12) United States Patent
Chiou et al.

(10) Patent No.: US 12,324,813 B2
(45) Date of Patent: Jun. 10, 2025

(54) METHOD AND PHARMACEUTICAL COMPOSITION FOR RESCUING RETINAL DEGENERATION

(71) Applicant: Taipei Veterans General Hospital, Taipei (TW)

(72) Inventors: Shih-Hwa Chiou, Taipei (TW); Shih-Jie Chou, Taipei (TW); Yueh Chien, Taipei (TW); Yi-Ping Yang, Taipei (TW)

(73) Assignee: TAIPEI VETERANS GENERAL HOSPITAL, Taipei (TW)

( * ) Notice: Subject to any disclaimer, the term of this patent is extended or adjusted under 35 U.S.C. 154(b) by 255 days.

(21) Appl. No.: 18/096,227

(22) Filed: Jan. 12, 2023

(65) Prior Publication Data
US 2024/0238334 A1 Jul. 18, 2024

(51) Int. Cl.
*A61K 33/18* (2006.01)
*A61K 31/136* (2006.01)

(52) U.S. Cl.
CPC ............ *A61K 33/18* (2013.01); *A61K 31/136* (2013.01)

(58) Field of Classification Search
CPC ............................... A61K 33/18; A61K 31/136
See application file for complete search history.

(56) References Cited

PUBLICATIONS

Chan, et al. "Reactive oxygen species-dependent mitochondrial dynamics and autophagy confer protective effects in retinal pigment epithelial cells against sodium iodate-induced cell death" 2019. Journal of Biomedical Science 26:40. doi:10.1186/s12929-019-0531-z (Year: 2019).*

Vo, et al. "Dusp6 is a genetic modifier of growth through enhanced ERK activity" 2019. Human Molecular Genetics 28:2. doi: 10.1093/hmg/ddy349 (Year: 2019).*

* cited by examiner

*Primary Examiner* — Frederick F Krass
*Assistant Examiner* — Toriana N. Vigil
(74) *Attorney, Agent, or Firm* — Birch, Stewart, Kolasch & Birch, LLP

(57) ABSTRACT

The present invention provides a method for rescuing retinal degeneration comprising administering a subject in need thereof a pharmaceutical composition comprising an inhibitor of DUSP6 via ERK 1/2 autophagy pathway.

2 Claims, 12 Drawing Sheets
(9 of 12 Drawing Sheet(s) Filed in Color)

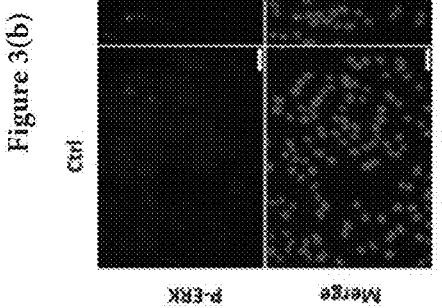
Figure 3(b)
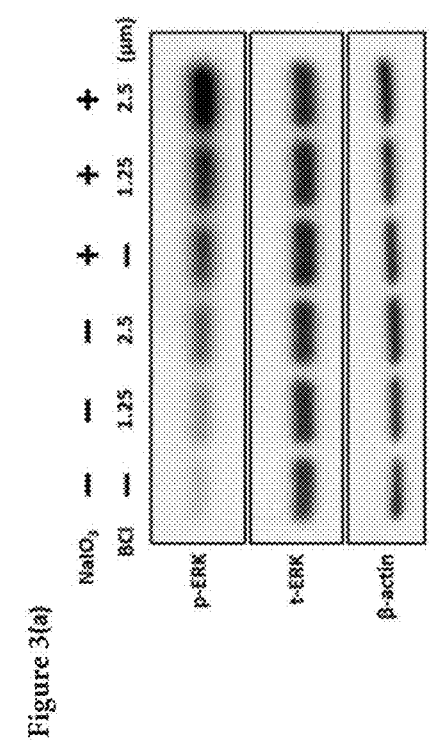
Figure 3(a)
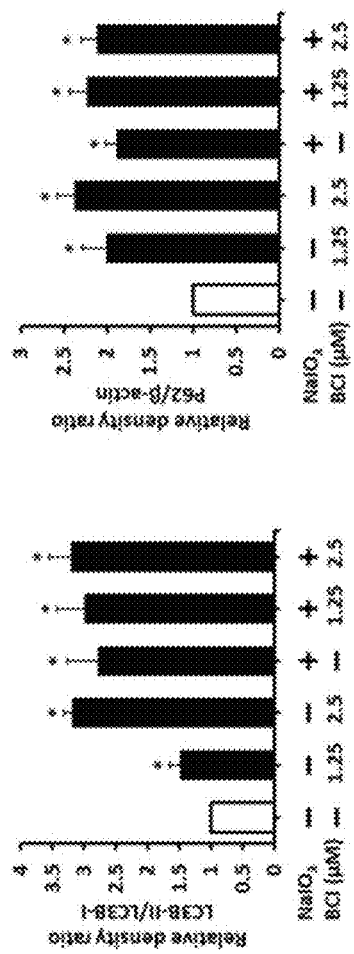
Figure 3(d)
Figure 3(e)
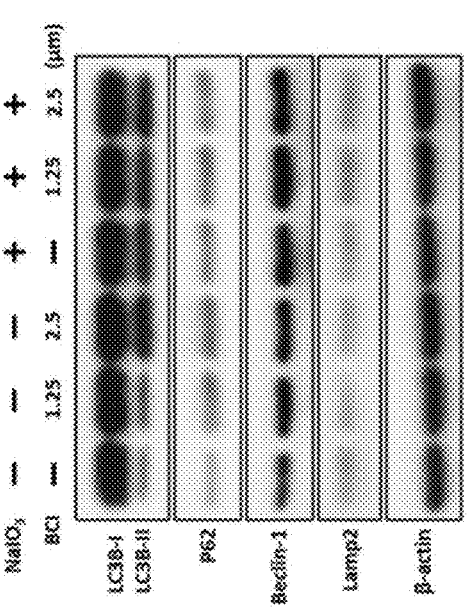
Figure 3(c)

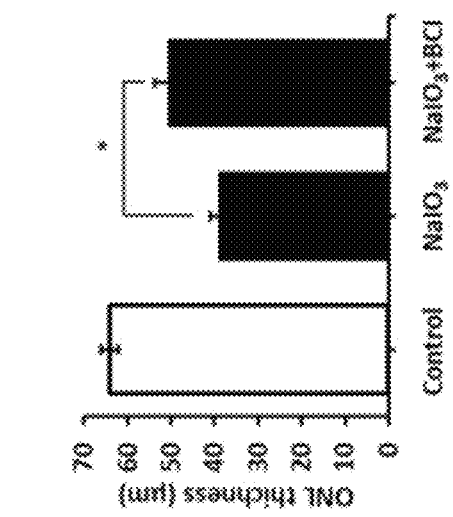
Figure 6(e)
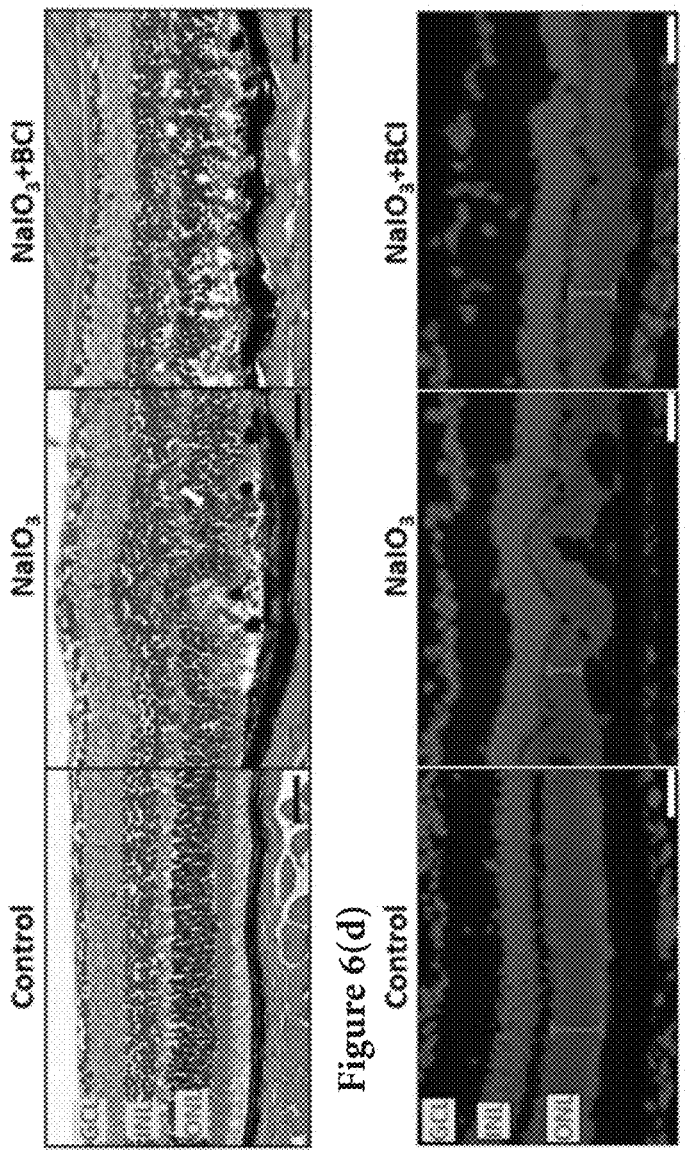
Figure 6(c)
Figure 6(d)

METHOD AND PHARMACEUTICAL COMPOSITION FOR RESCUING RETINAL DEGENERATION

FIELD OF THE INVENTION

The present invention pertains to a method and pharmaceutical composition for rescuing retinal degeneration.

BACKGROUND OF THE INVENTION

Retinal degeneration is the leading cause of central vision loss among the elderly population [1,2]. A systematic literature review further indicated the significance of this condition from a global perspective and predicted its increasing prevalence due to the exponential ageing of the population [3]. Despite the fact that aging is the primary risk factor in the course of retinal deterioration, it is also influenced by other factors, including genetic susceptibility and oxidative stress. Retina has become a target of oxidative stress, since it is constantly exposed to the light stimuli needed for vision [4]. Oxidative stress occurs when the ROS level surpasses a certain threshold, which leads to the onset of a protective mechanism in the cells such as autophagy [5]. Furthermore, excess ROS disrupt autophagy homeostasis and damages the retina at the molecular level, thus diminishing its structural and functional integrity. Under normal circumstances, retinal pigment epithelial cells (RPEs) play a critical role in neutralizing the harmful radicals to maintain a redox homeostasis state in the retina [4]. Furthermore, RPEs phagocytize toxic lipid-protein aggregates derived from the outer layer of photoreceptors via autophagy [6]. However, this constant exposure to oxidative stress will eventually shift these RPEs to an exhausted stage, hindering their proper and regular functions [7]. Owing to the detrimental role of oxidative stress in the destruction of the retinal structure, many researchers have used oxidizing compounds (e.g., sodium iodate ($NaIO_3$)) that can preferentially damage RPEs to generate in vitro and in vivo retinal degeneration disease models [8].

Autophagy is a catabolic process that removes unwanted or damaged cellular components via lysosomal digestion. Interestingly, several pieces of evidence have shown that autophagy is closely associated with oxidative stress [9,10]. Autophagy regulates cell biogenesis by recycling metabolic precursors and reduces oxidative stress by clearing toxic intracellular waste [11]. As mentioned, autophagy is crucial for cell homeostasis and in toxic lipid-protein aggregates metabolism in retinal physiology. However, autophagy dysregulation has been associated with increased susceptibility to oxidative stress, which may eventually lead to the progression of RPE degeneration in age-related macular degeneration (AMD) [12,13]. Research has shown that sodium iodate can induce autophagy in RPE cells, leading to decreased mitochondrial activity by mitophagy, which in turn affects cellular viability [14]. The autophagic flux process was also found to be partly blocked in $NaIO_3$-treated cells despite autophagy occurring [15]. Chan made the observation that the inhibition of autophagy in RPE cells enhances cell susceptibility to $NaIO_3$, while the activation of autophagy is able to counteract the cell death mechanisms induced by $NaIO_3$ [16].

The extracellular signal-related kinases (ERK1/2) are some of the main signaling pathways for the induction and maintenance of autophagy and regulate the maturation of autophagic vacuoles [18]. To be specific, there are three subfamilies in the ERK1/2 family: serine/threonine phosphatase (PP2A, PP2C), tyrosine phosphatases (STEP, HePTP, PTP-SL), and dual-specificity protein phosphatases (DUSPs) [19]. Among the DUSPs family, DUSP6 specifically interacts with ERK1/2 and plays a counterbalanced role in the downstream regulation of ERK 1/2 [20]. The inhibition of DUSP6 has been suggested to play a suppressive role in some diseases such as gastric or ovarian cancers [21]. Previous studies have also reported the upregulation of DUSP6 in response to external factors, including oxidative stress, and the participation of autophagy proteins (ATG) in regulation through the ERK1/2 pathway in many cell types [22]. Although the role of DUSP6 protein in ERK-mediated cell functions has been demonstrated in many cells, the relationship between DUSP6 and autophagy regulation in RPE cells under oxidative stress-induced cell death is still blurry.

Accordingly, it is desirable to develop an approach to secure rescuing the retinal pigment epithelium.

BRIEF SUMMARY OF THE INVENTION

It is unexpectedly discovered in the present invention that the regulation of Dual-specificity protein phosphatase 6 (DUSP6) rescues retinal degeneration via the ERK1/2 autophagy pathway both in vivo and in vitro retinal degeneration models.

In one aspect, the present invention provides a method for rescuing retinal degeneration comprising administering a subject in need thereof a pharmaceutical composition comprising an inhibitor of DUSP6 via ERK1/2 autophagy pathway.

In one embodiment of the invention, the inhibitor of DUSP6 is sodium iodate ($NaIO_3$) or (E/Z)-BCI hydrochloride (BCI).

In one example, the present invention provides a method for treating a retinal degeneration disease, comprising administering a subject in need thereof a pharmaceutical composition comprising a therapeutically effective amount of an inhibitor of DUSP6 and a pharmaceutically acceptable carrier, wherein the inhibitor of DUSP6 is sodium iodate or BCI.

In one example of the invention, the inhibitor is sodium iodate, which provides an effect in a significant increase in oxidative stress and autophagy.

In another example of the invention, the inhibitor of DUSP6 is (E/Z)-BCI hydrochloride (BCI), which provides a significant increase in the structural repair in the retinal layer in said subject.

It was found in the present invention that the inhibition of DUSP6 activity promoted autophagy flux through the ERK pathway via the upregulation of immunoblotting expression in ARPE-19 cell line and C57BL/6N mice to sodium iodate ($NaIO_3$) as an oxidative stress inducer, showing a significant increase in autophagic flux activities.

It was also found in the present invention that BCI provided an effect on the regulation of the ERK1/2 pathway in retinal degeneration models, particularly in significant increasing in the autophagic flux in vitro and structural repair in the retinal layer in vivo. It could be concluded that DUSP6 inhibition promotes autophagy flux activity through the upregulation of the ERK cascade.

It was confirmed in the invention that the retina layer was recovered after being treated with a DUSP6 inhibitor, $NaIO_3$ or BCI; which suggested that DUSP6 inhibitor can rescue retinal damage by restoring the mouse retina's autophagy flux. It is suggested that the upregulation of DUSP6 can cause autophagy flux malfunctions in the RPE, and the DUSP6 inhibitor can restore autophagy induction. Accordingly, a DUSP6 inhibitor could serve as a potential therapeutic approach for retinal degeneration disease.

In yet another aspect, the present invention also provides a pharmaceutical composition for treating a retinal degeneration disease comprising a therapeutically effective amount of an inhibitor of DUSP6 and a pharmaceutically acceptable carrier.

In a further aspect, the present invention also provides a use of an inhibitor of DUSP6 for manufacturing a treatment for treating a retinal degeneration disease, or an inhibitor of DUSP6 for use in the treatment of a retinal degeneration disease.

In one embodiment of the invention, the inhibitor of DUSP6 is sodium iodate.

In another embodiment of the invention, the inhibitor of DUSP6 is BCI.

The features and advantages of the present invention will be apparent to those skilled in the art. While numerous changes may be made by those skilled in the art, such changes are within the scope of this invention.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred.
The Drawings Include:

FIGS. 3(a)-3(g) show that BCI promotes autophagic flux via ERK pathway activity in ARPE-19 cells. (a) Representative immunoblotting analysis of p-ERK/ERK axis expression in ARPE-19 cells treated with 1.25 and 2.5 μM of BCI in oxidative conditions. (b) Immunocytochemistry staining showed the p-ERK signals in ARPE-19 cells with or without BCI treatment in oxidative conditions. Scale bar=50 μm. (c) Representative immunoblotting analysis showed the expression of autophagic relative proteins in AR-PE-19 cells treated with 1.25 and 2.5 μM BCI in oxidative conditions. (d,e) Quantitative analysis of immunoblotting. Representative data from three independent experiments are shown. *p<0.05. (f) Immunocytochemistry staining exhibited the LC3B and p62 expression levels in ARPE-19 cells with BCI (1.25 μM) treatment in oxidative conditions. Scale bar=50 μm. (g) Live-image of full-length LC3B (GFP) and cleavage form LC3B (RFP) expression level. Right subpanel represents the white boxed region of the image in the left subpanel with high magnification. Scale bar=20 μm.

FIGS. 6(a)-6(e) show that BCI activated autophagic flux via the upregulation of the ERK pathway in vivo. (a) Immunofluorescence staining of p-ERK in mice retinas with BCL treatment. 50 μm. (b) Immunofluorescence staining of LC3B and p62 in mice retinas with BCI treatment. 50 μm. (c) The morphology of mice retinas with BCI treatment was confirmed by H & E staining and (d) immunofluorescence staining. The red bar shows the thickness of the ONL layers. Scale bar=50 μm. (e) Retinal thickness was calculated using Image J. *p value<0.05 comparison to NaIO$_3$ group.

DETAILED DESCRIPTION OF THE INVENTION

Figure 1:
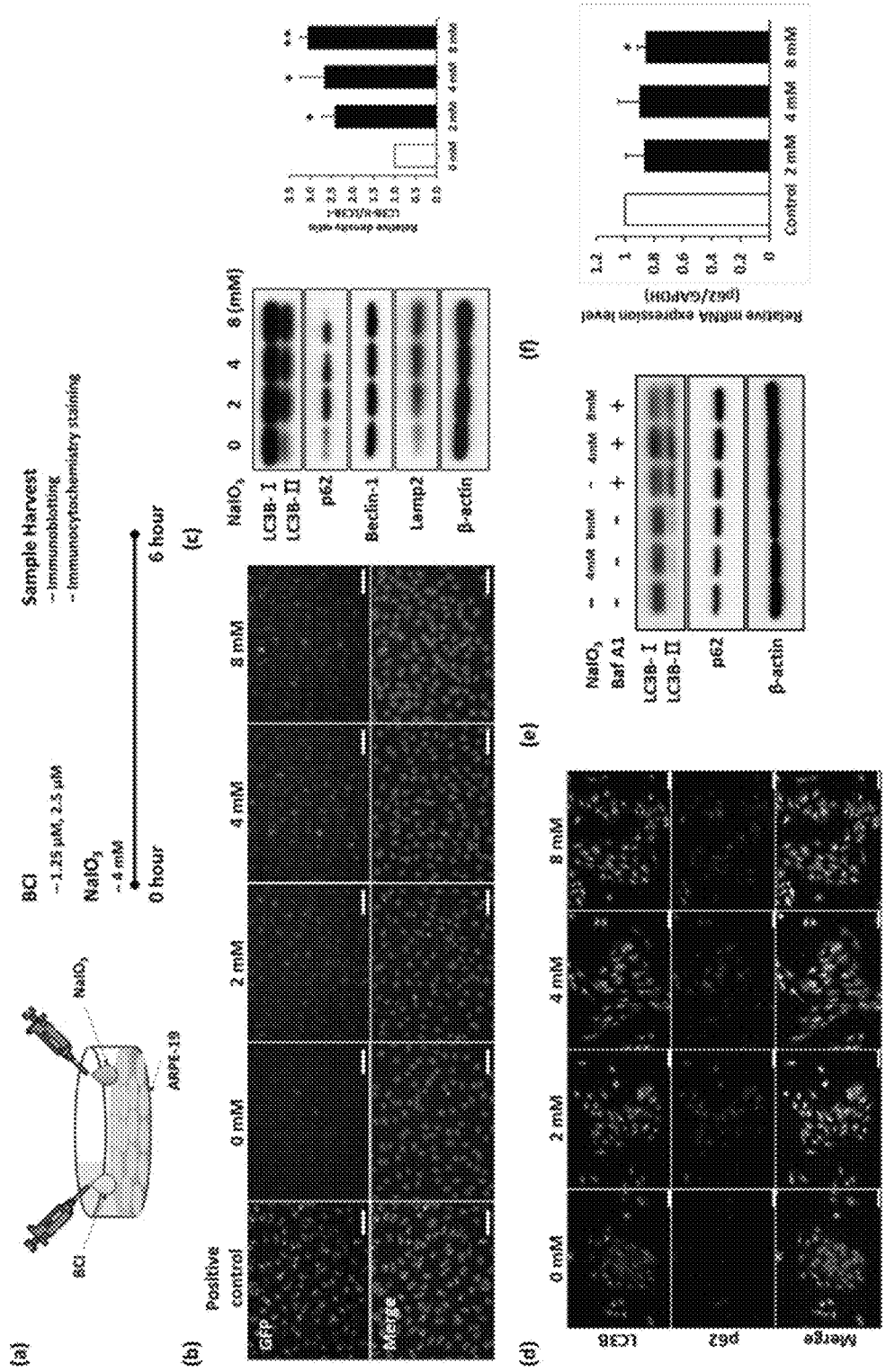
FIG. 1 shows the sodium iodate disrupted the autophagy flux in ARPE-19 cells. (a) Schematic showing the protocol of in vitro NaIO$_3$ treatment on ARPE-19 cells. (b) Autophagic vesicles in ARPE-19 cells with NaIO$_3$ treatment were detected using a autophagic detection kit. Scale bar=100 μm. (c) Representative blots analysis of autophagy relative protein expression after NaIO$_3$ treatment. Quantitative analysis of immunoblotting. (d) Immunocytochemistry staining of LC3B and p62 after NaIO$_3$ treatment in ARPE-19 cells. Nuclei were stained with DAPI. Scale bar=50 μm. (e) Representative blots analysis of autophagic flux relative protein expression under Baf-A1 treatment. (f) Real-time quantitative PCR showed an mRNA level of p62; n=3. Representative data from three independent experiments are shown. *p<0.05 and **p<0.01.

The foregoing summary, as well as the following detailed description of the invention, will be better understood when read in conjunction with the appended drawings. For the purpose of illustrating the invention, there are shown in the drawings embodiments which are presently preferred.

As used herein, the singular forms "a", "an", and "the" include plural referents unless the context clearly dictates otherwise. Thus, for example, reference to "a sample" includes a plurality of such samples and equivalents thereof known to those skilled in the art.

As used herein, the term "subject" refers to a human or a mammal, such as a patient, a companion animal (e.g., dog, cat, and the like), a farm animal (e.g., cow, sheep, pig, horse, and the like) or a laboratory animal (e.g., rat, mouse, guinea pig, and the like).

As used herein, the term "carrier" refers to a material commonly used on the formulation of a pharmaceutical composition used to enhance stability, sterility and deliverability. When the peptide delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. The compositions may contain physiologically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

As used herein, the term "pharmaceutically acceptable" refers to a substance without undue toxicity, irritant effects, allergic reactions or other problems or complications, which is suitable for use in human and/or animals.

As used herein, the term "therapeutically effective amount" refers to a subject treated at a reasonable risk-benefit ratio applicable to any medical treatment, which means an amount sufficient to confer a therapeutic effect on the therapeutic effect. In particular, a "therapeutically effective amount" refers to an amount for ameliorating the symptoms associated with the disease, preventing or delaying the onset of the disease, and/or reducing the severity of the symptoms of the disease. A therapeutically effective amount is generally administered in a dosage regimen that may include a plurality or unit doses. A therapeutically effective amount (and/or an appropriate unit dose in an effective dosage regimen) will depend, for example, on the route of administration, on the combination with other pharmaceutical agents The therapeutically effective amount will be varied by age, weight, general health, gender and diet of the subject to be treated, time of administration, route of administration, duration of treatment, and various factors, including similar factors well known in the art.

As used herein, the term "treatment" (also "treat" or "treating") refers to a particular disease or disorder, including partially or completely alleviate, ameliorate, inhibit, delay the onset of, reduce the severity of one or more symptoms or disease.

According to the invention, a method for rescuing retinal degeneration or treating a retinal degeneration disease, comprises administering a subject in need thereof a pharmaceutical composition comprising an inhibitor of DUSP6 via ERK1/2 autophagy pathway.

In some examples of the invention, the inhibitor of DUSP6 is sodium iodate (NaIO$_3$) or (E/Z)-BCI hydrochloride (BCI).

As used herein, the term "retinal degeneration disease," "retinal degeneration" or "degenerative retinal disease" refers to a progressive neurologic disorder caused by genetic mutations and/or environmental or pathologic damage to the retina, which is incurable so far.

In one example of the invention, the inhibitor of DUSP6 is sodium iodate, which was confirmed to exhibit a significant increase in oxidative stress and autophagy.

In another example of the invention, the inhibitor of DUSP6 is (E/Z)-BCI hydrochloride (BCI), which was confirmed to provide a significant increase in the structural repair in the retinal layer in said subject.

According to the invention, a DUSP6 inhibitor such as sodium iodate or BCI, could serve as a potential therapeutic approach for retinal degeneration disease through the upregulation of DUSP6 which can cause autophagy flux malfunctions in retinal pigment epithelium (RPE), and restore autophagy induction.

The present invention is further illustrated by the following examples, which are provided for the purpose of demonstration rather than limitation.

EXAMPLES

Materials and Methods 1.1 Cell Line and Cell Culture

ARPE-19 cells were purchased from ATCC (ATCC® CRL-2302™). Cells were cultured in Dulbecco's modified Eagle's medium (DMEM)/F-12 (Hyclone, Logan, UT, USA) supplemented with 10% FBS (Gibco, Grand Island, NY, USA), and 1% penicillin-Streptomycin (50 U/mL). Cells were passaged at 90% confluence and maintained at 37° C. and 5% CO2 with a 95% relative humidity.

1.2. Sodium Iodate and Protein Regulators

Treatment in ARPE-19 Cells were seeded at a density of 2×106 cells in 6 cm dishes for 24 h and treated with sodium iodate (NaIO$_3$) (Sigma, Saint Louis, MO, USA) at concentrations 0, 2, 4, and 8 mM for 6 h at 37° C. Cells were treated with the autophagy inhibitor Bafilomycin A1 (Sigma, Saint Louis, MO, USA) at 75 nM or DUSP6 inhibitor BCI (Sigma, Saint Louis, MO, USA) at 1.25 μM or 2.5 μM for 6 h at 37° C. Proteins were collected after treatment for further study.

1.3 Immunoblotting Analysis

C57BL/6N mice were sacrificed and their eyes were collected. The excess muscle tissue outside the sclera was removed and then a needle was used to make a hole in the cornea then remove the whole cornea. Next, we eliminated the lens and retina, and finally lysed the remaining tissue RIPA buffer (10× Merck Millipore, Temecula, CA, USA) containing with 1% protease inhibitor. Meanwhile, in vitro ARPE-19 cells were collected and lysed with RIPA buffer containing with 1% protease inhibitor. Subsequently, cell lysates were centrifuged for 10 min at 4° C. and the supernatants were collected. Next, the protein concentrations were measured via the BCA Protein Quantification Kit. An equal weight of total protein was separated by electrophoresis on SDS/PAGE. After the proteins were transferred onto polyvinylidene difluoride (PVDF) membranes (Millipore, Bedford, MA, USA), the membranes were incubated with blocking buffer (1×TBST and 5% skim milk) for 1 h at room temperature. After the blocking step, the membranes were incubated with the following primary antibodies at 4° C. overnight: DUSP6 (Abcam, Cambridge, UK), Phospho-ERK1/2 (Cell Signaling, Danvers, MA, USA), ERK1/2 (Cell Signaling, Danvers, MA, USA), LC3B (Novus, Centennial, CO, USA), SQSTM1/p62 (Abcam, Cambridge, UK), LAMP2 (Abcam, Cambridge, UK), Beclin-1 (Cell Signaling, Danvers, MA, USA), and Bactin (Sigma, Saint Louis, MO, USA). Next, membranes were washed three times with TBST and incubated with HRP-conjugated secondary antibodies including Goat anti-mouse IgG (Invitrogen, Carlsbad, CA, USA) and Goat anti-rabbit IgG (Invitrogen, Carlsbad, CA, USA) for 1 h at RT. The antigen-antibody complexes were detected by an enhanced chemiluminescence (ECL) substrate kit (Bioman, Millipore, Bedford, MA, USA). Bands were analyzed and quantified by the ImageJ (NIH, Bethesda, MD, USA) analysis software.

1.4. Autophagic Flux Assay

The cell autophagic flux was measured by the Autophagy Detection Kit (Abcam, Cambridge, UK). First, cells were pretreated with the autophagy inducer and chloroquine for 16 h as a positive control. After being treated with NaIO$_3$, the cells were washed twice with 1× assay buffer and 100 μL of Microscopy Dual Detection Reagent was added, which included green detection reagent and nuclear staining buffer. Samples were protected from light and incubated for 30 min at 37° C. Next, the cells were carefully rinsed with 100 μL 1× assay buffer and incubated for 20 min with 4% formaldehyde. After washing three times with 1× assay buffer, the stained cells were analyzed by wide-field fluorescence microscopy.

1.5. Quantitative Real Time Polymerase Chain Reaction (qRT-PCR)

The cDNA was diluted to 200 ng/μL with sterile water and mixed with SYBR PCR Master Mix and primers. Amplification reaction was performed in a thermal cycler according to the manufacturer's instructions. mRNA abundance was quantified using the threshold cycle method. The mRNA expression of GAPDH was used as an internal control for normalization.

1.6. 3(4,5. Dimethyl 2 Thiazolyl) 2,5 Diphenyl 2H Tetrazolium Bromide (MTT) Assay The MTT assay kit (Sigma, Saint Louis, MO, USA) was used for a cell viability test. ARPE-19 cells were plated at 5×104 cells per well into 96-well plates for 24 h and treated with different concentrations of $NaIO_3$ (0, 2, 4, 8, 16, 32 mM) for 6 h. Following treatment, the cells were washed in PBS and we added 10 μL of MTT working solution (5 mg/mL in phosphate buffer solution, Sigma, Saint Louis, MO, USA) for 4 h at 37° C. in a CO2 incubator. After incubation, 50 μL of DMSO (solubilizing reagent) was added to each well and then mixed by a micropipette. The presence of viable cells was visualized by the development of a purple color due to the formation of formazan crystals. Finally, the intensity was measured by the reading of OD540 on a microplate spectrophotometer (Tecan Austria GmbH 5082, Grobdig, Austria).

1.7. ROS Detection Assay (DHR-123 Assay)

Intracellular ROS was measured by the fluorescent probe dihydrorhodamine 123 (DHR-123) (Invitrogen, Carlsbad, CA, USA) to examine DHR-123 changes to rhodamine 123 (Rh-123) when oxidized by ROS. First, the ARPE-19 cells were plated at 5×105 cells per well into 24-well plates for 24 h. Sodium iodate ($NaIO_3$) was dissolved in Dimethyl Sulfoxide (DMSO). After treatment with different concentrations (0, 2, 4, 8 mM) of $NaIO_3$ for 6 h, the cells were incubated with 2 μM DHR-123 dye for 30 min in the dark in 5% CO2 at 37° C. with a 95% relative humidity. Then, the fluorescence intensity of Rh-123 was measured by a fluorescence microscope (Olympus America, Melville, NY, USA) at a 488 nm excitation wavelength.

1.8. Animal

Healthy male C57BL/6N mice (8-week-old, about 20 g) were purchased from LASCO. The mice were housed under standard conditions of a 12:12 h dark-light cycle with access to standard rodent chow and water ad libitum. For each experimental group, 3 mice were used for the experiments. All the mice were treated according to the guidelines of the Association for Research in Vision and Ophthalmology (ARVO) Statement on Use of Animals in Ophthalmic and Vision Research, animal study was approved by Institutional Animal Care and Use Committee of Taipei Veteran General Hospital (IACUC), approval number: 2020-038 (1 Jan. 2020).

1.9. Retinal Degeneration Model Established with Sodium Iodate Treatment by Intraperitoneal Injection The sodium iodate solution (Sigma, Saint Louis, MO, USA) was diluted with PBS for AMD mimic model in vivo. The final concentration was 30 mg/kg for mice treatment and they were injected by intraperitoneal injection. The mice were then sacrificed and the mouse eyes were collected at different stages for further histological analyses. Following this established model, the protective effect of the DUSP inhibitor will be demonstrated through intravitreal injection and real-time image observation.

1.10. Histological Assessment of the Retina

Retina samples were fixed with 4% paraformaldehyde (Sigma, Saint Louis, MO, USA) overnight, followed by 1×PBS. The methodology used for fixation, dehydration, clearing, infiltration, and embedding was developed according to that of Bio-Check Laboratories. Briefly, each retina sample was sectioned into 3 μm slices using vibratome (Leica, Buffalo Grove, IL, USA), followed by hematoxylin and eosin (H & E) staining. The morphology of the retina was observed using a light microscope (Olympus America, Melville, NY, USA). Next, the thicknesses of the retina, defined as the distance between the inner limiting membrane, Bruch's membrane, and the outer nuclear layer (ONL), were measured by Image J (NIH, Bethesda, Maryland, USA).

1.11. Fundoscopy & Optical Coherence Tomography

After anesthesia with a mixed solution of Zoletil (50 mg/kg) and Ropum (10 mg/kg), a mouse retinal structure image was obtained with multi-contrast optical coherence tomography (OCT), according to previous reports [23]. The fundus photography images were acquired with a retinal imaging camera (Nikon, Shinagawa, Tokyo, Japan). Fundoscopy and OCT images were captured on the exact retinal space surrounding the optic nerve.

1.12. Immunofluorescence Staining

In vitro, the cells were seeded in 24-well plates at a density of 2×105 per well and incubated at 37° C. with 5% CO2 for 24 h. Following treatment with 4 mM of $NaIO_3$ for 6 h, the cells were washed twice with PBS and then fixed with 4% paraformaldehyde (PFA) (Sigma, Saint Louis, MO, USA) for 15 min. After rinsing three times with PBS, the cells were permeabilized and blocked with a blocking solution (0.3% BSA and 0.1% Triton X-100 in PBS) at room temperature for 1 h. After blocking, cells were incubated with primary antibodies overnight at 4° C. The primary antibodies include DUSP6 (Abcam, Cambridge, UK), Phospho-ERK1/2 (Cell Signaling, Danvers, MA, USA), LC3B (Novus, Centennial, CO, USA), and SQSTM1/p62 (Abcam, Cambridge, UK). After incubation, cells were washed three times with PBST (0.1% Triton X-100 in PBS). Secondary antibodies (1:700) were applied for 3 h at room temperature. The secondary antibodies include IgG Alexa 488 goat anti-rabbit IgG and Alexa 594 goat anti-mouse IgG. Nuclei were stained with DAPI (1:1000) for 10 min at 4° C. and slides were observed by a light microscope (Olympus America, Melville, NY, USA). In vivo, the sample slices were pretreated with bleaching solution (1% NaH2PO4 and 2.5% H2O2) overnight at room temperature. Next, the primary antibodies, including DUSP6, Phospho-ERK1/2, LC3B, SQSTM1/p62, and RPE65, were incubated with the sample slices overnight at 4° C. After incubation, the samples were washed three times with PBST. Tests with secondary antibodies (1:700) were conducted for 1 h at room temperature. The secondary antibodies included IgG Alexa 488 goat anti-rabbit IgG and Alexa 594 goat anti-mouse IgG. After treating them with mounting solution, the slides were observed by a fluorescence microscope (Olympus America, Melville, NY, USA).

1.13. DUSP6 Inhibitor Treatment in Mice

Mice were divided into three groups: a control group, $NaIO_3$ group, and BCI group. Mice in the BCI group were given $NaIO_3$ at a dose of 30 mg/kg by intraperitoneal injection for 4 days and then given BCI (0.5 mg/kg) for 3 days through intravitreal injection. All the healthy controls received intra-peritoneal placebo injection and the NaIO$_3$ group received the intra-vitreous placebo injection. The structure of the retina was analyzed by real-time images and H & E staining. Proteins were collected from retina for further study.

1.14. Statistical Analysis

The experiment data are presented as means±SEMs. The normative distribution of the data was determined through the Kolmogorov-Smirnov test and non-parametric values were analyzed using the Mann-Whitney test. For statistical analysis, one-way analysis of variance (ANOVA) and Student's t-test were performed; $p<0.05$ was taken as significant, and highly significant differences in the statistics were accepted if $p<0.01$.

2. Results 2.1. Sodium Iodate Disrupted the Autophagy Flux in ARPE-19 Cells

RPE malfunction is one of the major pathological characteristics of retinal degeneration, and autophagy is an important lysosomal degradation process that can remove damaged organelles and misfolded proteins in retinas. However, the mechanism of retinal degeneration remains unclear, and whether autophagy plays a role in it is still poorly understood. To investigate the pathological mechanism of retinal degeneration, ARPE-19 cells, which have been widely applied in studying retinal pathology, were exposed to sodium iodate (NaIO$_3$), an oxidative induction reagent, to establish retinal degeneration models. To assess the expression of autophagic markers in RPE cells under the impact of NaIO$_3$-induced stress, ARPE-19 cells were treated with different concentrations of NaIO$_3$ (0, 2, 4, 8 mM) for 6 h (FIG. 1(a)). We observed that NaIO$_3$ induced the generation of autophagic vesicles in a dose-dependent manner (FIG. 1(b)). To further examine the expression levels of autophagic marker under NaIO$_3$ treatment, the total proteins were collected and subjected to an immunoblotting analysis. As demonstrated in FIG. 1c, autophagic markers including LC3B-II, Beclin-1, and LAMP2 were gradually upregulated in NaIO$_3$-treated cells. Furthermore, an increase in LC3B-positive speckles was also observed in the NaIO$_3$-treated group, indicating autophagosome generation (FIG. 1(d)). These data indicate the impact of NaIO$_3$ on inducing autophagy in RPE cells.

Based on the immunoblotting and immunofluorescence staining data, we found that the expression of the autophagic marker p62 (p62/SQSTM1) is increased after NaIO$_3$ treatment. p62 protein, a well-known substrate of selective autophagy, interacts with LC3B, resulting in the degradation of ubiquitinated substrates followed by its degradation in the autophagosome. However, the accumulation of p62 has previously been shown to be associated with the deficiency of autophagic flux under oxidative stress [24]. To further check the autophagic flux in RPE cells, the autophagic inhibitor Bafilomycin A1 (Baf-A1) was used to evaluate the cell response in NaIO$_3$-treated ARPE-19 cells. Baf-A1 treatment led to an increase in LC3B-II expression in a dose-dependent manner, indicating the early stages of autophagy (FIG. 1(e)). Meanwhile, the p62 expression levels remained unchanged despite the Baf-A1 treatment. Furthermore, NaIO$_3$ treatment at any given dose did not affect the p62 mRNA level compared to the control ARPE-19 cells (FIG. 1(f)). These results indicated that the elevated p62 expression induced by NaIO$_3$ is not due to the disruption of proteasome activities or the upregulation of the p62 gene. Therefore, NaIO$_3$ may have an effect on blocking late-stage autophagic flux in ARPE-19 cells.

Figure 2:
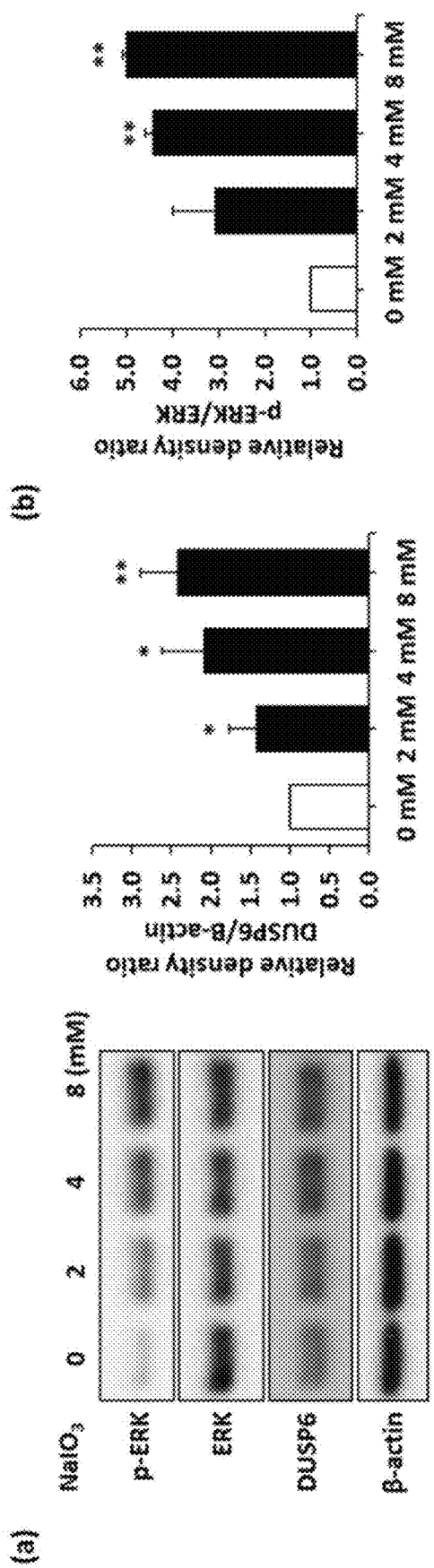
FIG. 2 shows the upregulation of DUSP6 and MAPK after NaIO$_3$ treatment. (a) Representative blots of DUSP6/p-ERK axis expression in ARPE-19 cells after NaIO$_3$ treatment and the quantitative analysis of the DUSP6 expression level. (b) Quantitative analysis of the p-ERK level. Representative data from three independent experiments are shown. *p<0.05 and **p<0.01.

2.2. NaIO$_3$ Treatment Induces DUSP6 and MAPK Upregulation In the model of retinal degeneration induced by the exposure of ARPE-19 cells to oxidized low-density lipoprotein (oxLDL), DUSP6 was found to be elevated in response to oxLDL treatment [25]. However, the treatment effect of NaIO$_3$ on the expression of DUSP6 and the role of DUSP6 in autophagic flux in retinal degeneration remain unclear. Hence, we sought to investigate DUSP6 expression and its role in autophagic flux in RPE cells under NaIO$_3$ treatment. An immunoblotting assay was conducted to examine the expression of DUSP6 and modulated kinase (p-ERK). The results indicated that DUSP6 expression was upregulated by NaIO$_3$ treatment in a dose-dependent manner (FIG. 2(a)). In addition, the p-ERK/ERK ratio, which represents the ERK activity, was also increased (FIG. 2(b)). These data suggest that the DUSP6 and ERK pathways were stimulated by NaIO$_3$ treatment in ARPE-19 cells. Collectively, these data indicate that DUSP6 expression was induced by the increased ERK activity in ARPE-19 cells under NaIO$_3$ treatment.

2.3. BCI Promotes the Autophagic Flux Via ERK Pathway Activity in ARPE-19 Cells

To investigate whether the inhibition of DUSP6 activity could regulate the autophagic flux against oxidative stress, we incubated ARPE-19 cells with NaIO$_3$ in the presence or absence of BCI, the DUSP6 inhibitor, for a period of 6 h. Next, we analyzed the autophagic flux through an immunoblotting assay and immunocytochemistry analysis. The p-ERK/ERK ratio, which represents the ERK activity, was significantly increased in NaIO$_3$-treated cells after BCI treatment in a dose-dependent manner (FIG. 3(a)). Consistently, immunofluorescence staining showed that the speckles of p-ERK were increased after BCI treatment, despite the presence or absence of NaIO$_3$ (FIG. 3b). This result indicated that BCI stimulates p-ERK signaling under both normal and NaIO$_3$-treated conditions.

Moreover, the late stage of autophagic flux was examined using immunoblotting and immunocytochemistry staining. The immunoblotting showed the upregulation of autophagic markers upon BCI treatment in a dose-dependent manner (FIG. 3c). The ratio of LC3B-II/LC3B-I is shown in FIG. 3d, while the quantification of p62 is displayed in FIG. 3e. In addition, the fluorescence images reveal the aggregation of autophagosomes in the BCI-treated group. Moreover, the perinuclear p62 punctate, which represents intensive autophagic activity, was significantly upregulated in NaIO$_3$ and BCI co-treated cells (FIG. 3(f)).

Figure 3G:
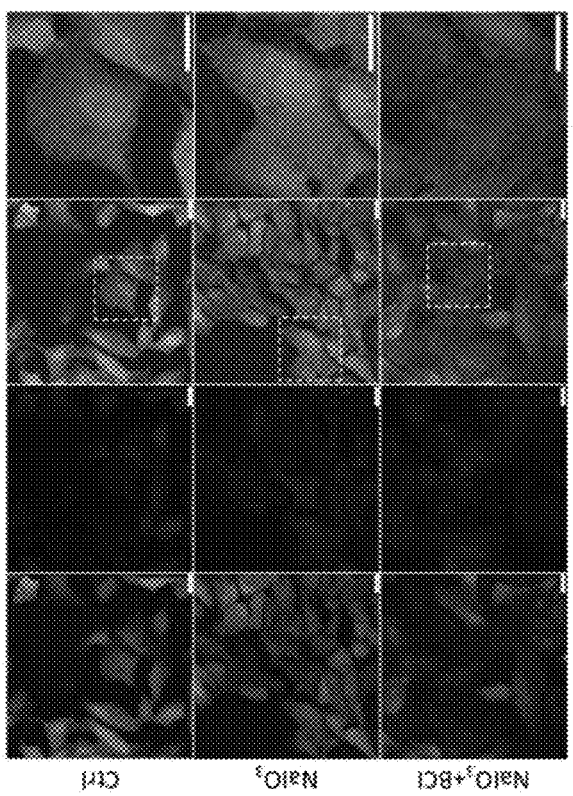
Figure 3F:
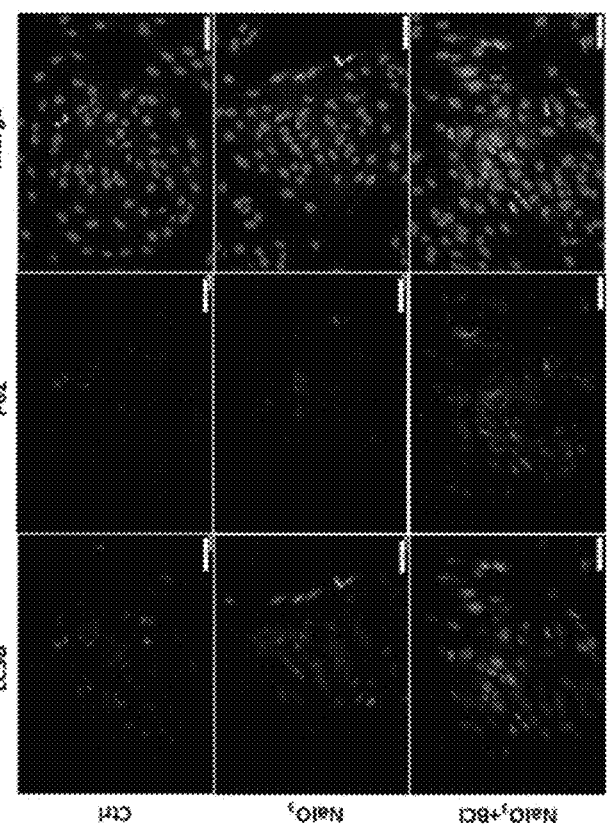

Furthermore, to estimate the autophagic flux in BCI-treated ARPE-19 cells, we introduced the GFP-LC3-RFP-LC3AG gene into ARPE-19 cells and monitored live images taken after BCI treatment. We observed that the number of GFP-positive puncta increased under NaIO$_3$-induced oxidative stress, presenting a low autophagic flux. Interestingly, treatment with BCI led to the GFP-positive signal being shifted to an RFP-positive signal, indicating the induction of late-stage autophagy by BCI treatment (FIG. 3g). Next, qPCR analysis showed that the mRNA level of p62 was upregulated in the BCI group, indicating that BCI could promote autophagic gene expression under oxidative stress in RPE cells, showing that BCI upregulated the p62 mRNA level under oxidative stress. ARPE-19 cells were co-treated with BCI and NaIO$_3$ for 6 hours and the mRNA levels of p62 were detected by qPCR. The positive effect of BCI in autophagic proteins signified that BCI effectively promoted autophagic flux through the blocking of DUSP6 activity to stimulate the p-ERK-mediated autophagy pathway. Taken together, these results suggest that the pharmacological activation of p-ERK by BCI could accelerate the autophagosome formation and the degradation of oxidative waste products in response to the oxidative stress induced by $NaIO_3$.

Figure 4A:
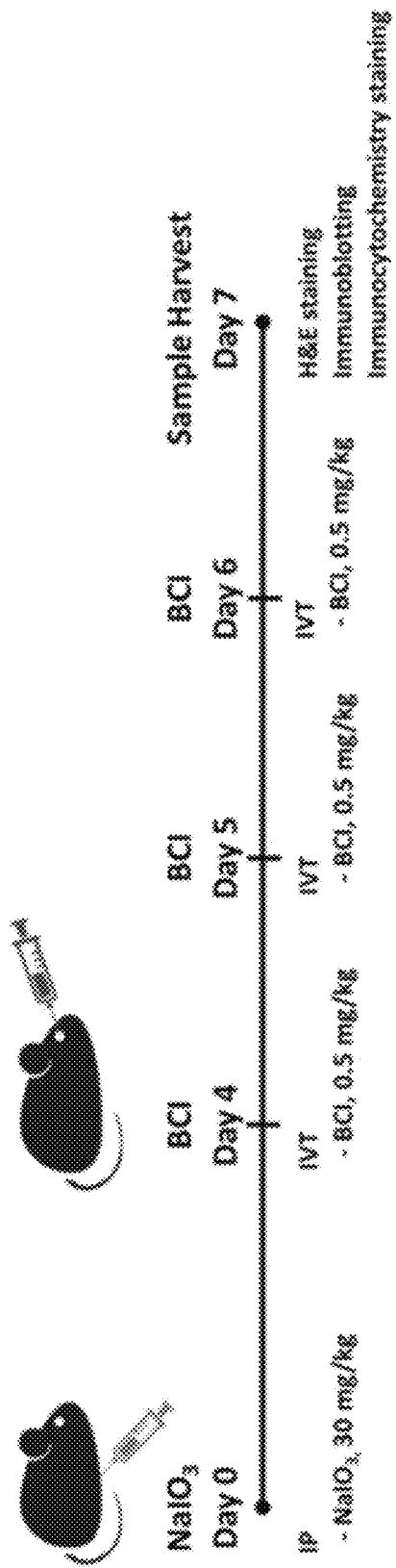
FIGS. 4(a)-4(f) show that DUSP6/p-ERK axis was upregulated in NaIO$_3$-induced retinal degeneration in vivo. (a) Schematic diagram illustrating the drug treatment and tissue preparation. (b) Real-time funds and retinal structures at different times post NaIO$_3$ injection were observed by fundoscopy and OCT system. The red arrows indicate the irregulated structure on the RPE layer. Representative data from three independent experiments are shown. (c) H & E staining presenting the mice retinal structures after treatment with NaIO$_3$. The abnormal deposits on the RPE layer is represented by the red arrows. Scale bar=50 μm. (d) Representative blots showed the DUSP6/p-ERK axis expression level after NaIO$_3$ injection in C57BL/6 mice. (e,f) A quantitative analysis is shown in (d). *p<0.05.
Figure 4C:
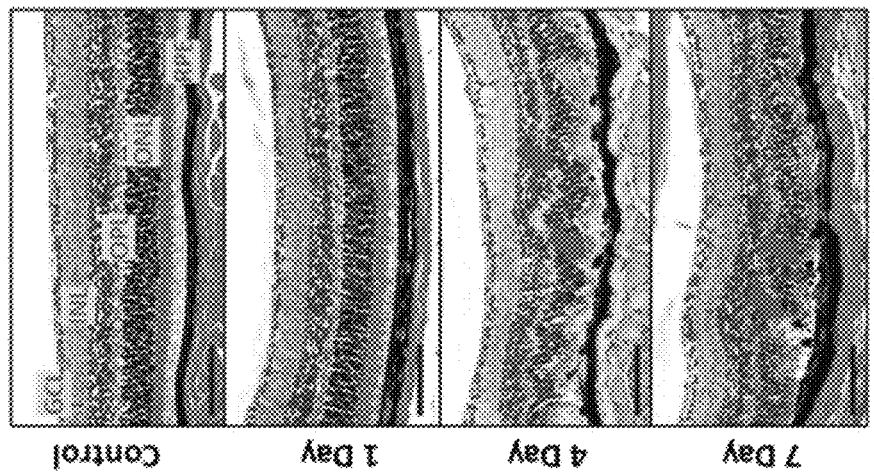
Figure 4B:
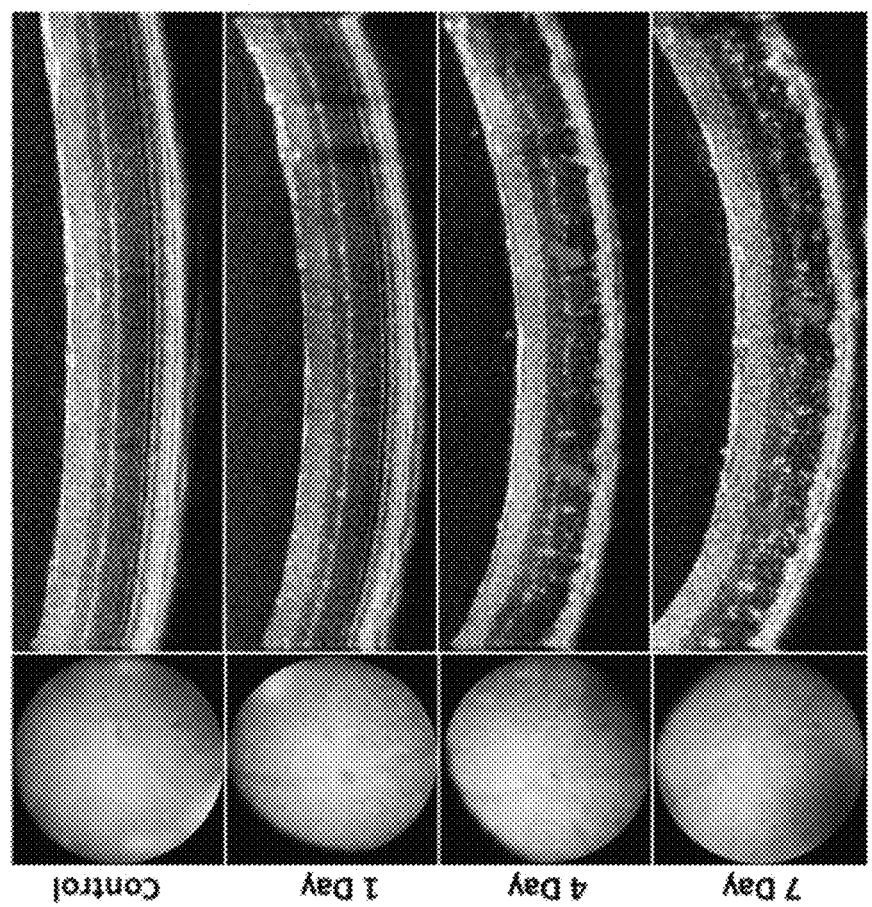

2.4. DUSP6/p-ERK Axis are Upregulated in $NaIO_3$-Induced Retinal Degeneration In Vivo $NaIO_3$ has been widely used to induce RPE degeneration in vivo owing to its RPE targeted oxidative damage [26]. However, the pathogenesis of RPE degeneration under the $NaIO_3$-induced oxidative model is still unclear. To investigate the relationship between autophagy regulation and oxidative stress in vivo, we treated wild-type C57BL/6 mice with $NaIO_3$ via an intravenous injection, followed by carrying out a retinal analysis of ultrahigh-resolution multicontrast optical coherence tomography (OCT) images and post-mortem histopathological sections for 1 week (FIG. 4(a)). Abnormal deposits of migratory cells in the RPE layer (red arrows) were observed 4 days post-injection, and these escalated within 7 days (FIG. 4(a)). The retina became thinner with the indistinct boundaries in different layers. In addition, the boundaries between the outer nuclear layer (ONL) and inner nuclear layer (INL) almost disappeared (FIG. 4(b)).

The effects of $NaIO_3$ on the retinal structure were further assessed by the hematoxylin and eosin (H & E) staining of retina tissue. In the control mice treated with saline, the retina showed the well-organized and clear boundary of retinal layers, including the ganglion cell layer (GCL), INL, and ONL. The retinal pigment epithelium (RPE) layer was smooth with even pigmentation, implying that the cells were in a healthy condition (FIG. 4(c)). One day after injection with $NaIO_3$, the retinal layers still remained regimented and showed a slightly melanin thicker morphology (FIG. 4(c)). It is worth noting that the arrangement of ONL was significantly disorganized 4 days after the $NaIO_3$ injection. In addition, the uneven pigmentation in the RPE layer indicated the degeneration of RPE (FIG. 4(c)). Seven days after injection, the inner segment/outer segment junction showed severe disruption above the RPE layer. Meanwhile, the migration of RPE cells was clearly observed with the severe melanin accretion (FIG. 4(c)). Furthermore, the retina became notably thinner due to the severe degeneration of photoreceptors and the RPE layer (FIG. 4(c)). Taken together, this histopathological study demonstrated that the $NaIO_3$ injection disrupted the retinal layer arrangement and induced severe pigmentation, accompanied with the accumulation of migratory cells and cell debris. Tight junction marker ZO-1 was used to validate the cell-cell junctions before and after treatment with $NaIO_3$. Our results have shown that the cell-cell junction was damaged after cells were treated with $NaIO_3$ compared to the control group, showing that cell-cell junctions were damaged after treated with $NaIO_3$ and co-treated with BCI rescue the cell-cell junction between RPE cells. The histological examination of ocular specimens was performed, and we found that after treatment with $NaIO_3$ the RPE layer had swelling and there had been a migration of pigmented cells into the OS layer. Based on previous studies, we suggest that the aggregation of cells was caused by the proliferation of microglials, and our data showed the Iba1 expression between the ONL and RPE layers, showing that the immunohistochemical examinations of the expression of Iba1 in $NaIO_3$-treated mice retina. Representative immunohistochemical staining for Iba-1 and DAPI 7 days after 30 mg/kg $NaIO_3$ injection. [27,28]. These findings successfully established a retinal degeneration disease model.

Figure 4E:
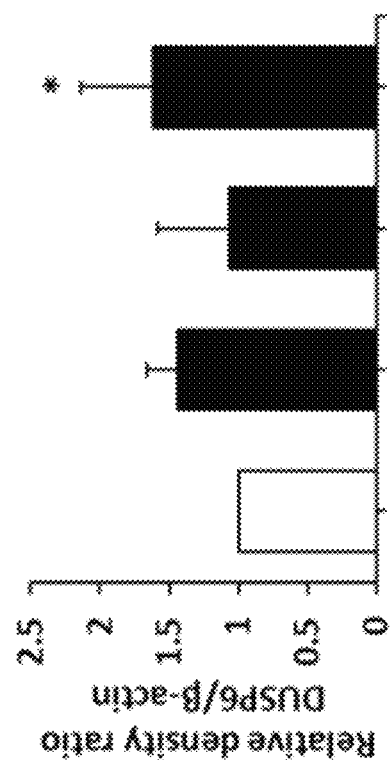
Figure 4F:
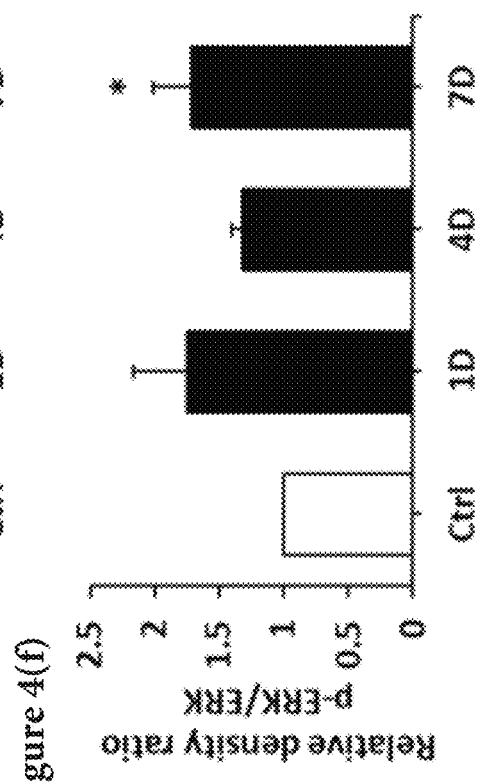
Figure 4D:
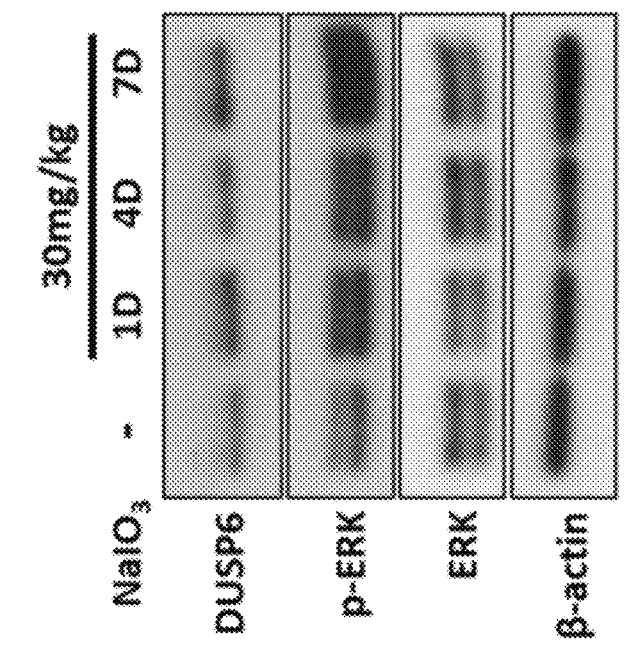

To identify the role of DUSP6 in response to oxidative stress in this retinal degeneration model, we collected eyeballs from the $NaIO_3$-treated mice at different time points and examined the DUSP6 protein expression in the retina after $NaIO_3$ treatment. The immunoblotting assays showed the upregulation of DUSP6 1 and 7 days after $NaIO_3$ treatment. The expression of phosphorylated ERK was also significantly upregulated, especially at 7 days post-injection (FIG. 4(d)). The quantification DUSP6, ERK, and phosphorylated ERK expression is shown in FIGS. 4(e) and 4(f). In brief, we demonstrated that the DUSP6/ERK axis was upregulated in the mouse retina under $NaIO_3$-induced oxidative stress, and this axis may play a critical role in the regulatory mechanism of retinal degeneration.

Figure 5B:
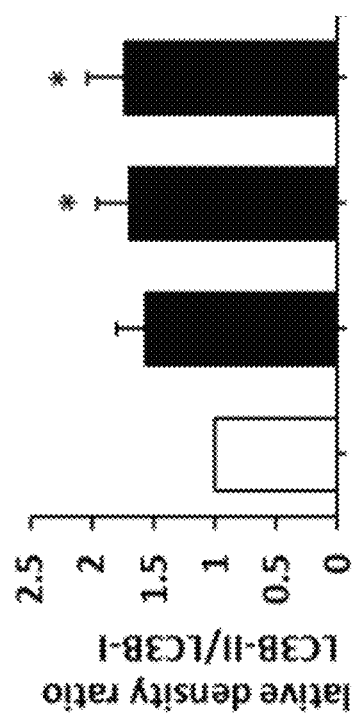
FIGS. 5(a)-5(d) show Autophagy relative genes are upregulated in NaIO$_3$-induced retinal degeneration in vivo. (a) Representative blots showed autophagy relative markers after the NaIO$_3$ injection of C57BL/6 mice. (b,c) Quantitative analysis of the Western blot. *p value<0.05 in comparison to control. (d) LC3B and p62 expression levels in the retinas of mice given NaIO$_3$ injections were observed via immunofluorescence staining. Scale bars=50 μm.
Figure 5C:
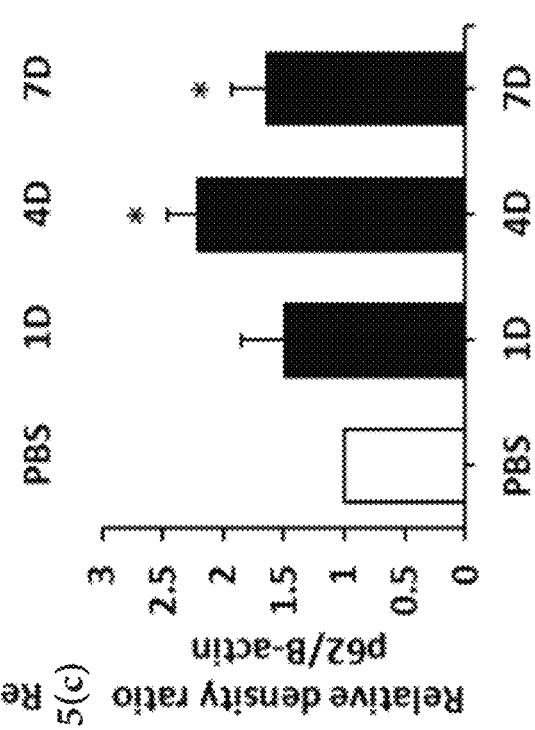
Figure 5A:
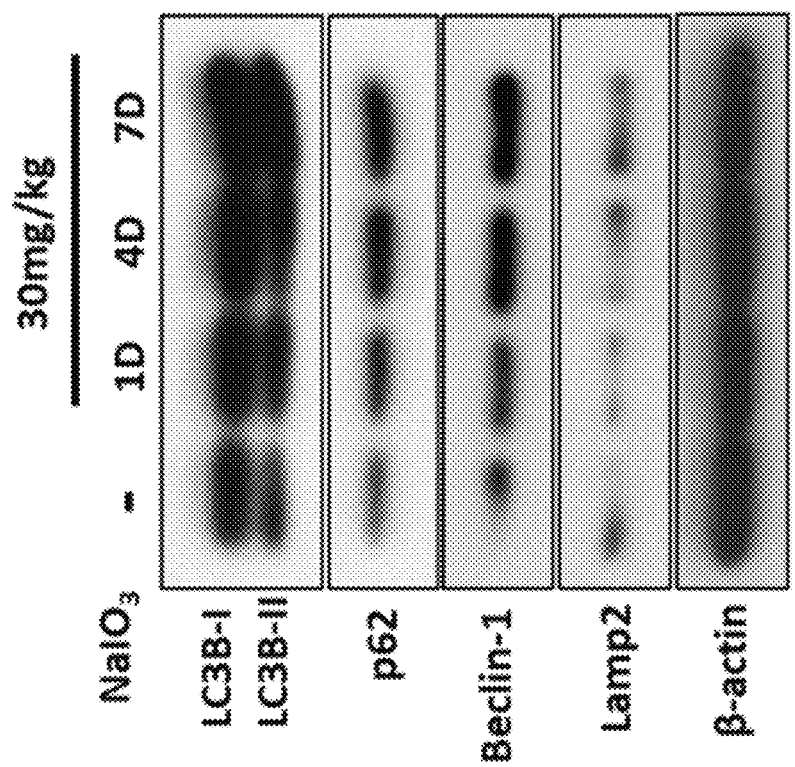
Figure 5D:
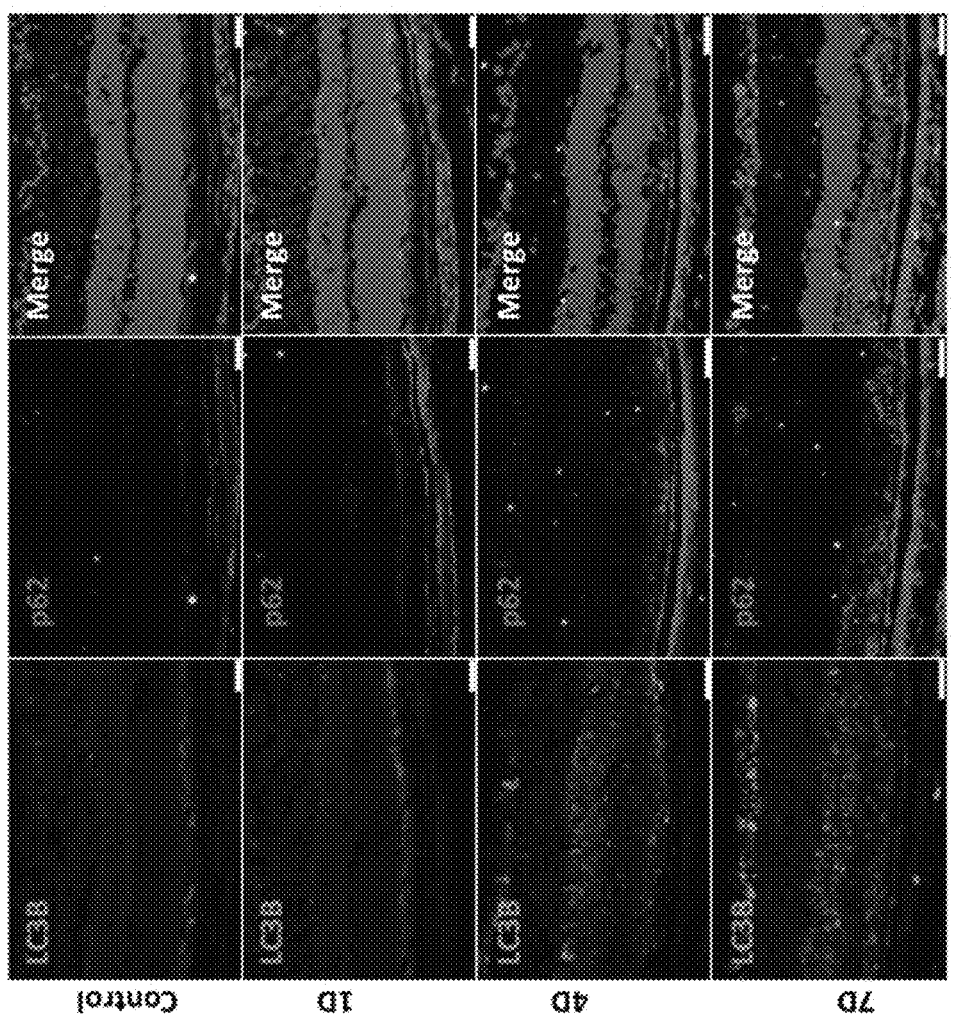

2.5. The Expression of Autophagic Markers are Increased in Retinal Degeneration Model Furthermore, to validate the autophagic flux in the $NaIO_3$-induced retinal degeneration model in vivo, immunoblotting and immunofluorescence staining were performed. Immunoblotting analysis showed that the autophagic markers LC3B-II, p62, and Beclin-1 were all upregulated after the course of $NaIO_3$ treatment (FIG. 5(a)). Quantitative data showed a significant increase in LC3B-II expression under $NaIO_3$
    induced oxidative stress (FIG. 5(b), 5(c)). This result indicated autophagosome accumulation, demonstrating the initial activation of autophagic flux. The upregulation of p62 expression further represented the characteristics of autophagic flux (FIG. 5(a), 5(c)). Furthermore, immunofluorescence staining showed an elevated expression of LC3B in different retinal layers of $NaIO_3$-treated mice, while p62 upregulation was predominantly found in photoreceptors and RPE layers (FIG. 5(d)). These findings showed that $NaIO_3$ can efficiently boost autophagic flux in the retina, particularly in the RPE cells.

2.6. BCI Activated the Autophagic Flux Via ERK Pathway Upregulation In Vivo

Figure 6A:
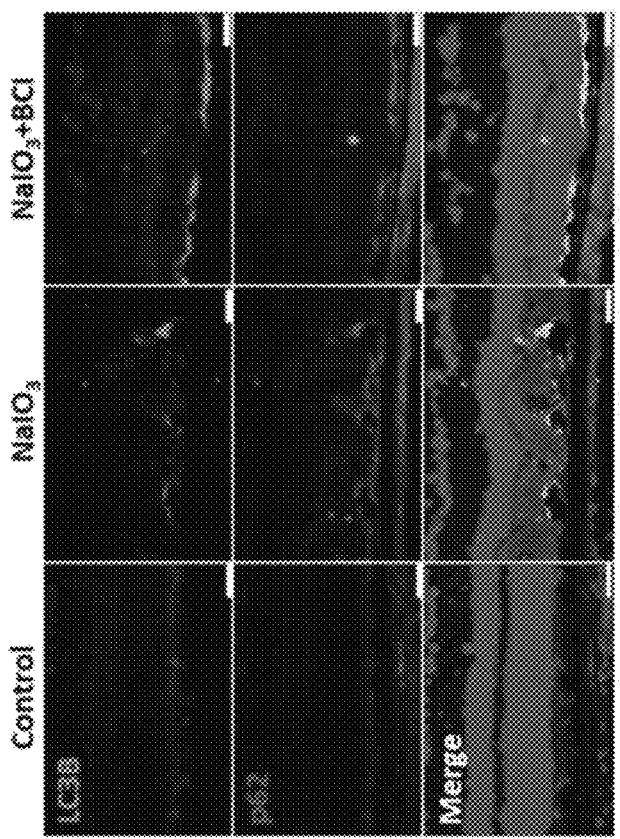
Figure 6B:
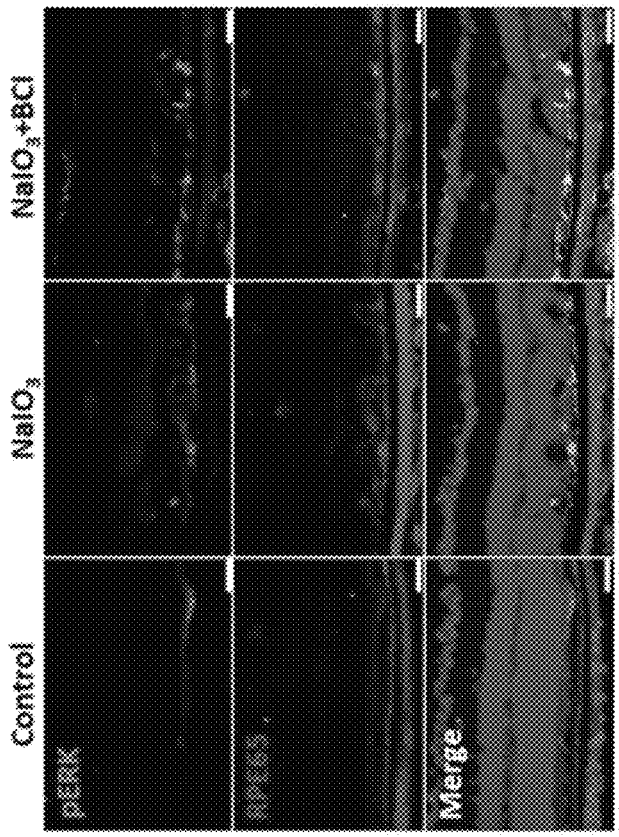

Based on our observations, the inhibition of DUSP6 activity using BCI could activate autophagic flux via the upregulation of 62 mRNA expression in vitro. To confirm the protein diversification and signal pattern in mouse retinas after BCI treatment under $NaIO_3$ induction, retinal sections were analyzed by immunofluorescence staining. We found that the phosphorylated ERK speckles around the ONL and RPE layers were increased in oxidative conditions and dramatically enhanced after BCI treatment (FIG. 6(a)). This result indicated that BCI upregulates the ERK activity in mouse retinas, especially in photoreceptors and RPE cells. Moreover, the excessive co-localization of LC3B and p62 between the ONL and RPE layers was observed in the BCI-treated group, indicating the higher autophagy activity in photoreceptor and RPE cells (FIG. 6(b)). In brief, these findings indicated that, under oxidative stress, the BCI treatment induced phosphorylated ERK activity and autophagic flux in mouse retinas, especially in photoreceptor and RPE cells. To further investigate the protective effect of BCI treatment in vivo against $NaIO_3$-induced oxidative damage, we conducted a histological examination and showed that the ONL boundary was significantly disorganized after the melanin deposition (FIG. 6c, red arrows). Migratory cells were observed in ONL in the $NaIO_3$-treated group, indicating the cell-cell junction loss of RPE under oxidative stress (FIG. 6(c)). In the BCI group, the ONL disorganization was alleviated by BCI treatment in the presence of NaIO$_3$-induced oxidative stress. The melanin deposition on the retina was also significantly reduced compared to that in the retinas of mice treated with NaIO$_3$ only (FIG. 6(c)). Moreover, immunofluorescence staining revealed that BCI treatment restored the ONL thickness, which was decreased by the thinner ONL after the NaIO$_3$ treatment. These results indicate the protective effect of BCI in retinal cells (FIG. 6(d), 6(e)). Collectively, our findings show that the inhibition of DUSP6 protects against retinal degeneration through promoting autophagic flux under NaIO$_3$-induced oxidative stress 3. Discussion The irreversible progression of retinal degeneration involves both inherited and acquired traits and ultimately causes cell death within the RPE layer and might result in blindness. Age-related macular degeneration (AMD) is the most common cause of retinal degeneration and is characterized by either the degradation of RPE cells (dry AMD) or choroidal neovascularization (wet AMD) [29]. In addition, other factors, including oxidative stress, inflammation, and hypoxia, can also cause retinal degeneration [13]. The exposure of RPE cells to oxidative stress results in the death of RPE cells and recapitulates the pathogenesis of AMD as a disease model. However, the underlying molecular mechanisms contributing to the progression of this disease, such as ROS-mediated signaling pathways, mitochondrial function, and autophagy, are yet to be investigated. To answer this question, we established a retinal degeneration model using NaIO$_3$; an oxidative inducer on the RPE cell line, ARPE-19; and a mouse model, C57BL/6N. The mouse model received a single intraperitoneal injection of 30 mg/kg of NaIO$_3$. These results showed that NaIO$_3$ treatment caused extensive damage to the RPE cells and disrupt the mouse retina structures, especially in the RPE layer. Autophagy-related proteins play a key role in autophagy, as they are the most tightly regulated components of the pathway. Beclin-1 regulates autophagy initiation and the lapidated form of microtubule-associated protein light chain 3-II (LC3-II) [29]. The lapidated form of microtubule-associated protein light chain 3-II (LC3-II) has been shown to be a reliable marker for completed autophagosomes. In addition, LAMP2 plays a critical role during the formation of lysosomes. Our immunoblotting data demonstrate elevated autophagy at multiple levels. First, the increase in Beclin-1, LC3-II, and LAMP2 protein expression indicates an increase in early autophagic flux in RPE cells under oxidative stress. Second, the phosphorylation of ERK protein was shown to be higher in NaIO$_3$-treated RPE cells than in control RPE cells, hinting that RPE undergoes autophagy impairment. Notably, it is demonstrated in the present invention that DUSP6 acts as a negative regulator of the ERK pathway by decreasing the autophagic response in NaIO$_3$-treated RPE cells. A further novel finding in the present invention is that BCI's inhibition of DUSP6 activity could promote autophagic flux and restore the retinal structure. The inhibition of autophagic flux is typically associated with aggregates or inclusion bodies positive for ubiquitin and associated with large perinuclear aggregates [31]. The impaired autophagy process has also been demonstrated in other neurodegenerative diseases, including Alzheimer's disease, Parkinson's disease, and Huntington's disease [32]. The protein p62, also called sequestosome (SQSTM1), a protein that is itself degraded by autophagy, may act as a link between ubiquitinated proteins and the autophagic machinery, thus facilitating their degradation in the lysosome. p62 accumulates when autophagy is inhibited, and when autophagy is induced p62 levels decrease, suggesting that p62 may be used as an autophagic flux reporter. Planned comparisons revealed that the accumulation of p62 was significantly decreased in mouse retinas treated with BCI, which suggested the restoration of autophagic flux in RPE cells. The mitogen-activated protein kinase (MAPK) pathway translates signals from mitogens into signals that regulate transcription and affect cell proliferation, differentiation, and apoptosis through the activation of protein kinase cascades [33]. Extracellular signal regulated protein kinase (ERK1/2) is a member of the MAPK family that plays a critical role in delivering extracellular signals to the nucleus, as well as regulating cell proliferation, cell differentiation, and the cell cycle [34]. Research indicates that ERK 1/2 is closely related to visual cycle regulation and plays a critical role in the survival of RPE and photoreceptor cells [35]. It is suggested that the MAPK/ERK signal transduction pathways may be involved in the reduced activity of autophagy in RPE cells on the nitrite-modified extracellular matrix (ECM). In the present invention, the regulation of NaIO$_3$-induced autophagy was found in an ERK1/2-dependent manner. This pattern of results is consistent with the previous literature, and we found that autophagy is involved in the NaIO$_3$-induced upregulation of stress proteins LC3B and p62 and the activation of the ERK pathway [36]. These data suggest that the ERK 1/2 pathway activates autophagic flux, which contributes to a possible survival mechanism under the oxidative stress condition.

Figure 7:
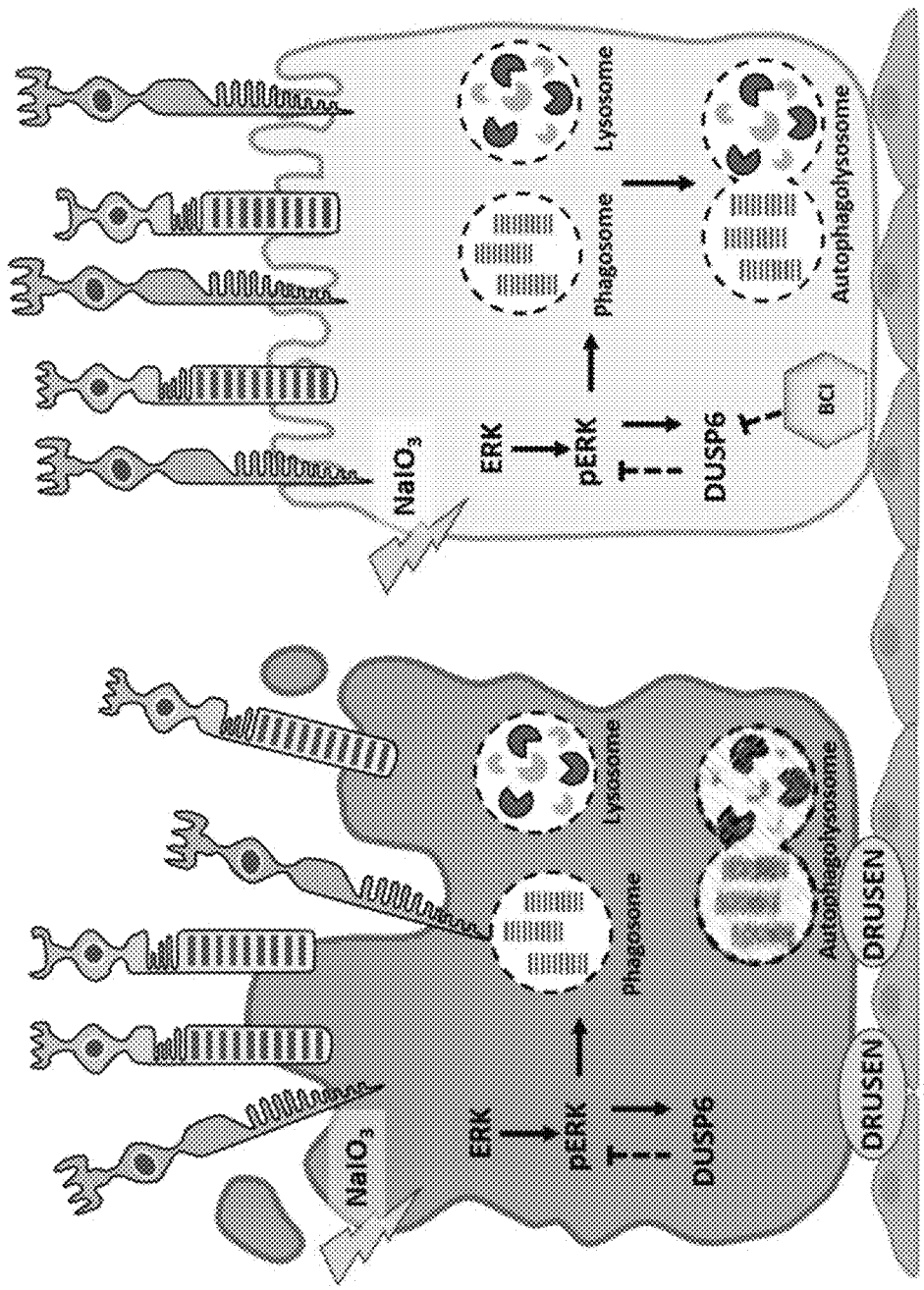
FIG. 7 illustrates the conclusion, demonstrating that the inhibition of DUSP6 could protect RPE and the retina against NaIO$_3$-induced oxidative stress-mediated autophagy dysfunction involving the ERK signaling pathway.

It is found in the present invention that the NaIO$_3$-mediated ERK/p-ERK pathway upregulates the DUSP6 expression level in RPE cells, and that the inhibition of DUSP6 could rescue the impaired autophagy. These findings represent the regulatory mechanism of the DUSP6/ERK axis in retinal cells. To further confirm the role of DUSP6 in ERK-mediated autophagy in retinal cells, BCI was used to inhibit the DUSP6 activity to promote autophagic flux. Interestingly, it is found that the p-ERK/ERK ratio was significantly increased upon BCI treatment, accompanied by the upregulation of autophagic markers in a dose-dependent manner. Furthermore, BCI treatment resulted in an elevated amount of p62 punctate around the cell nucleus in RPE cells under oxidative stress. In addition, the p62 mRNA level was upregulated following BCI treatment compared to the cells only treated with NaIO$_3$. In accordance with these findings, other autophagy markers, including LC3B, Beclin-1, and Lamp2, were also upregulated by BCI treatment in NaIO$_3$-treated cells. It was further confirmed these data through the live imaging of NaIO$_3$-treated RPE cells in a retinal degeneration model. The data demonstrated a significant increase in LC3B-II upon BCI treatment, indicating the inhibition of autophagic flux by DUSP6 under oxidative stress conditions. These findings suggest that BCI may counteract the hazardous effect of oxidative stress in RPE cells via ERK1/2-mediated autophagy upregulation, offering clues for developing novel interventional strategies during disease states by restoring autophagic flux and preventing RPE cell dysfunction induced by oxidative stress. 5. Conclusions In summary, the results from this study demonstrated that NaIO$_3$ is an oxidant that can activate the ERK1/2 pathway and that the regulation of DUSP6 leads to suspending autophagic flux in RPE cells. Treatment with the DUSP6 inhibitor BCI modulates the autophagy activity and provides novel therapeutic help to restore autophagic flux and prevent retinal degeneration induced by oxidative stress (FIG. 7).

REFERENCES

1. Rim, T. H.; Kawasaki, R.; Tham, Y. C.; Kang, S. W.; Ruamviboonsuk, P.; Bikbov, M. M.; Miyake, M.; Hao, J.;

1. Fletcher, A.; Sasaki, M.; et al. Prevalence and Pattern of Geographic Atrophy in Asia: The Asian Eye Epidemiology Consortium. Ophthalmology 2020, 127, 1371-1381. [CrossRef] [PubMed]
2. Li, J. Q.; Welchowski, T.; Schmid, M.; Mauschitz, M. M.; Holz, F. G.; Finger, R. P. Prevalence and incidence of age-related macular degeneration in Europe: A systematic review and meta-analysis. Br. J. Ophthalmol. 2020, 104, 1077-1084. [CrossRef] [PubMed]
3. Wong, W. L.; Su, X.; Li, X.; Cheung, C. M. G.; Klein, R.; Cheng, C. Y.; Wong, T. Y. Global prevalence of age-related macular degeneration and disease burden projection for 2020 and 2040: A systematic review and meta-analysis. Lancet Glob. Health 2014, 2, e106-e116. [CrossRef]
4. Domenech, E. B.; Marfany, G. The Relevance of Oxidative Stress in the Pathogenesis and Therapy of Retinal Dystrophies. Antioxidants 2020, 9, 347. [CrossRef] [PubMed]
5. Yun, H. R.; Jo, Y. H.; Kim, J.; Shin, Y.; Kim, S. S.; Choi, T. G. Roles of Autophagy in Oxidative Stress. Int. J. Mol. Sci. 2020, 21, 3289. [CrossRef]
6. Intartaglia, D.; Giamundo, G.; Conte, I. Autophagy in the retinal pigment epithelium: A new vision and future challenges. FEBS J. 2021. [CrossRef]
7. Datta, S.; Cano, M.; Ebrahimi, K.; Wang, L.; Handa, J. T. The impact of oxidative stress and inflammation on RPE degeneration in non-neovascular AMD. Prog. Retin. Eye Res. 2017, 60, 201-218. [CrossRef]
8. Hanus, J.; Anderson, C.; Sarraf, D.; Ma, J.; Wang, S. Retinal pigment epithelial cell necroptosis in response to sodium iodate. Cell Death Discov. 2016, 2, 16054. [CrossRef]
9. Ornatowski, W.; Lu, Q.; Yegambaram, M.; Garcia, A. E.; Zemskov, E. A.; Maltepe, E.; Fineman, J. R.; Wang, T.; Black, S. M. Complex interplay between autophagy and oxidative stress in the development of pulmonary disease. Redox Biol. 2020, 36, 101679. [CrossRef]
10. Zhuang, X. X.; Wang, S. F.; Tan, Y.; Song, J. X.; Zhu, Z.; Wang, Z. Y.; Wu, M. Y.; Cai, C. Z.; Huang, Z. J.; Tan, J. Q.; et al. Pharmacological enhancement of TFEB-mediated autophagy alleviated neuronal death in oxidative stress-induced Parkinson's disease models. Cell Death Dis. 2020, 11, 128. [CrossRef]
11. Moreno, M. L.; Merida, S.; Bosch-Morell, F.; Miranda, M.; Villar, V. M. Autophagy Dysfunction and Oxidative Stress, Two Related Mechanisms Implicated in Retinitis Pigmentosa. Front. Physiol. 2018, 9, 1008. [CrossRef]
12. Mitter, S. K.; Song, C.; Qi, X.; Mao, H.; Rao, H.; Akin, D.; Lewin, A.; Grant, M.; Dunn, W., Jr.; Ding, J.; et al. Dysregulated autophagy in the RPE is associated with increased susceptibility to oxidative stress and AMD. Autophagy 2014, 10, 1989-2005. [CrossRef]
13. Trachsel-Moncho, L.; Benlloch-Navarro, S.; Fernandez-Carbonell, A.; Ramirez-Lamelas, D. T.; Olivar, T.; Silvestre, D.; Poch, E.; Miranda, M. Oxidative stress and autophagy-related changes during retinal degeneration and development. Cell Death Dis. 2018, 9, 812. [CrossRef]
14. Zhang, X. Y.; Ng, T. K.; Brelen, M. E.; Wu, D.; Wang, J. X.; Chan, K. P.; Yung, J. S. Y.; Cao, D.; Wang, Y.; Zhang, S.; et al. Continuous exposure to non-lethal doses of sodium iodate induces retinal pigment epithelial cell dysfunction. Sci. Rep. 2016, 6, 37279. [CrossRef]
15. Lin, Y. C.; Horng, L. Y.; Sung, H. C.; Wu, R. T. Sodium Iodate Disrupted the Mitochondrial-Lysosomal Axis in Cultured Retinal Pigment Epithelial Cells. J. Ocul. Pharmacol. Ther. 2018, 34, 500-511. [CrossRef]
16. Chan, C. M.; Huang, D. Y.; Sekar, P.; Hsu, S. H.; Lin, W. W. Reactive oxygen species-dependent mitochondrial dynamics and autophagy confer protective effects in retinal pigment epithelial cells against sodium iodate-induced cell death. J. Biomed. Sci. 2019, 26, 40. [CrossRef]
17. Kochetkova, E. Y.; Blinova, G. I.; Zubova, S. G.; Bykova, T. V.; Pospelov, V. A.; Pospelova, T. V. Mek/Erk-Pathway is Required to Maintain Cytoprotective Autophagy Process in Irradiated Ela+Cha-Ras Transformants. Tsitologiia 2016, 58, 947-954.
18. Dagda, R. K.; Zhu, J.; Kulich, S. M.; Chu, C. T. Mitochondrially localized ERK2 regulates mitophagy and autophagic cell stress: Implications for Parkinson's disease. Autophagy 2008, 4, 770-782. [CrossRef]
19. Theodosiou, A.; Ashworth, A. MAP kinase phosphatases. Genome Biol. 2002, 3, reviews3009. [CrossRef]
20. Ahmad, M. K.; Abdollah, N. A.; Shafie, N. H.; Yusof, N. M.; Razak, S. R. A. Dual-specificity phosphatase 6 (DUSP6): A review of its molecular characteristics and clinical relevance in cancer. Cancer Biol. Med. 2018, 15, 14-28. [CrossRef]
21. Wu, Q. N.; Liao, Y. F.; Lu, Y. X.; Wang, Y.; Lu, J. H.; Zeng, Z. L.; Huang, Q. T.; Sheng, H.; Yun, J. P.; Xie, D.; et al. Pharmacological inhibition of DUSP6 suppresses gastric cancer growth and metastasis and overcomes cisplatin resistance. Cancer Lett. 2018, 412, 243-255. [CrossRef]
22. Martinez-Lopez, N.; Athonvarangkul, D.; Mishall, P.; Sahu, S.; Singh, R. Autophagy proteins regulate ERK phosphorylation. Nat. Commun. 2013, 4, 2799. [CrossRef]
23. Syu, J. P.; Buddhakosai, W.; Chen, S. J.; Ke, C. C.; Chiou, S. H.; Kuo, W. C. Supercontinuum source-based multi-contrast optical coherence tomography for rat retina imaging. Biomed. Opt. Express 2018, 9, 6132-6144. [CrossRef]
24. Lamark, T.; Svenning, S.; Johansen, T. Regulation of selective autophagy: The p62/SQSTM1 paradigm. Essays Biochem. 2017, 61, 609-624. [CrossRef]
25. Yamada, Y.; Tian, J.; Yang, Y.; Cutler, R. G.; Wu, T.; Telljohann, R. S.; Mattson, M. P.; Handa, J. T. Oxidized low density lipoproteins induce a pathologic response by retinal pigmented epithelial cells. J. Neurochem. 2008, 105, 1187-1197. [CrossRef]
26. Chowers, G.; Cohen, M.; Marks-Ohana, D.; Stika, S.; Eijzenberg, A.; Banin, E.; Obolensky, A. Course of Sodium Iodate-Induced Retinal Degeneration in Albino and Pigmented Mice. Investig. Ophthalmol. Vis. Sci. 2017, 58, 2239-2249. [CrossRef]
27. Wang, J.; Iacovelli, J.; Spencer, C.; Saint-Geniez, M. Direct effect of sodium iodate on neurosensory retina. Investig. Ophthalmol. Vis. Sci. 2014, 55, 1941-1953. [CrossRef]
28. Moriguchi, M.; Nakamura, S.; Inoue, Y.; Nishinaka, A.; Nakamura, M.; Shimazawa, M.; Hara, H. Irreversible Photoreceptors and RPE Cells Damage by Intravenous Sodium Iodate in Mice Is Related to Macrophage Accumulation. Investig. Ophthalmol. Vis. Sci. 2018, 59, 3476-3487. [CrossRef] [PubMed]
29. Garcia-Onrubia, L.; Valentin-Bravo, F. J.; Coco-Martin, R. M.; Gonzalez-Sarmiento, R.; Pastor, J. C.; Usategui-Martin, R.; Pastor Idoate, S. Matrix Metalloproteinases in Age-Related Macular Degeneration (AMD). Int. J. Mol. Sci. 2020, 21, 5934. [CrossRef] [PubMed]

30. Bhore, N.; Wang, B. J.; Chen, Y. W.; Liao, Y. F. Critical Roles of Dual-Specificity Phosphatases in Neuronal Proteostasis and Neurological Diseases. Int. J. Mol. Sci. 2017, 18, 1963. [CrossRef] [PubMed]
31. Wong, E.; Bejarano, E.; Rakshit, M.; Lee, K.; Hanson, H. H.; Zaarur, N.; Phillips, G. R.; Sherman, M. Y.; Cuervo, A. M. Molecular determinants of selective clearance of protein inclusions by autophagy. Nat. Commun. 2012, 3, 1240. [CrossRef]
32. Kiriyama, Y.; Nochi, H. The Function of Autophagy in Neurodegenerative Diseases. Int. J. Mol. Sci. 2015, 16, 26797-26812. [CrossRef]
33. Kyosseva, S. V. Targeting MAPK Signaling in Age-Related Macular Degeneration. Ophthalmol. Eye Dis. 2016, 8, 23-30. [CrossRef]
34. Zou, J.; Lei, T.; Guo, P.; Yu, J.; Xu, Q.; Luo, Y.; Ke, R.; Huang, D. Mechanisms shaping the role of ERK 1/2 in cellular senescence (Review). Mol. Med. Rep. 2019, 19, 759-770. [CrossRef]
35. Aung, K. H.; Liu, H.; Ke, Z.; Jiang, S.; Huang, J. Glabridin Attenuates the Retinal Degeneration Induced by Sodium Iodate In Vitro and In Vivo. Front. Pharmacol. 2020, 11, 566699. [CrossRef]
36. Ferreira-Marques, M.; Carvalho, A.; Cavadas, C.; Aveleira, C. A. PI3K/AKT/MTOR and ERK1/2-MAPK signaling pathways are involved in autophagy stimulation induced by caloric restriction or caloric restriction mimetics in cortical neurons. Aging 2021, 13, 7872-7882. [CrossRef]
37. Kauppinen, A.; Kaarniranta, K.; Salminen, A. Potential Role of Myeloid-Derived Suppressor Cells (MDSCs) in Age-Related Macular Degeneration (AMD). Front. Immunol. 2020, 11, 384. [CrossRef]
38. Zhang, F.; Tang, B.; Zhang, Z.; Xu, D.; Ma, G. DUSP6 Inhibitor (E/Z)-BCI Hydrochloride Attenuates Lipopolysaccharide-Induced Inflammatory Responses in Murine Macrophage Cells via Activating the Nrf2 Signaling Axis and Inhibiting the NF-kappaB Pathway. Inflammation 2019, 42, 672-681. [CrossRef]
39. Ramkissoon, A.; Chaney, K. E.; Milewski, D.; Williams, K. B.; Williams, R. L.; Choi, K.; Miller, A.; Kalin, T. V.; Pressey, J. G.; Szabo, S.; et al. Targeted Inhibition of the Dual Specificity Phosphatases DUSP1 and DUSP6 Suppress MPNST Growth via JNK. Clin. Cancer Res. 2019, 25, 4117-4127. [CrossRef]

What is claimed is:

1. A method for structural repair in the retinal layer of a subject suffering from a retinal degeneration comprising administering to a subject in need thereof a pharmaceutical composition comprising an inhibitor of DUSP6 and a pharmaceutically acceptable carrier.

2. The method of claim 1, wherein the inhibitor of DUSP6 is (E/Z)-BCI hydrochloride (BCI).

* * * * *